(12) United States Patent
Rinecker et al.

(10) Patent No.: US 8,242,458 B2
(45) Date of Patent: Aug. 14, 2012

(54) IRRADIATION SYSTEM AND IRRADIATION METHOD

(75) Inventors: Hans Rinecker, Munich (DE); Joerg Hauffe, Munich (DE)

(73) Assignee: AD Verwaltungs-GmbH & Co. KG, Gruenwald (DE)

( * ) Notice: Subject to any disclaimer, the term of this patent is extended or adjusted under 35 U.S.C. 154(b) by 357 days.

(21) Appl. No.: 12/580,761

(22) Filed: Oct. 16, 2009

(65) Prior Publication Data

US 2010/0117002 A1    May 13, 2010

(30) Foreign Application Priority Data

Oct. 17, 2008  (EP) .................................. 08166918

(51) Int. Cl.
*A61N 5/00* (2006.01)
*G21K 5/00* (2006.01)
(52) U.S. Cl. ..................... 250/398; 250/492.3
(58) Field of Classification Search ............... 250/398, 250/400, 453.11, 492.1, 492.3
See application file for complete search history.

(56) References Cited

U.S. PATENT DOCUMENTS

| | | | |
|---|---|---|---|
| 6,265,837 B1 | 7/2001 | Akiyama et al. | |
| 6,433,349 B2* | 8/2002 | Akiyama et al. | 250/505.1 |
| 6,509,573 B1 | 1/2003 | Badura et al. | |
| 6,614,038 B1* | 9/2003 | Brand et al. | 250/492.3 |
| 6,639,234 B1* | 10/2003 | Badura et al. | 250/492.3 |
| 7,838,855 B2* | 11/2010 | Fujii et al. | 250/505.1 |
| 2006/0027766 A1* | 2/2006 | Matsuda et al. | 250/496.1 |
| 2006/0058637 A1 | 3/2006 | Sommer | |
| 2008/0067452 A1* | 3/2008 | Moriyama et al. | 250/503.1 |

FOREIGN PATENT DOCUMENTS

| | | |
|---|---|---|
| EP | 0 978 294 | 2/2000 |
| EP | 1 625 876 | 2/2006 |
| WO | WO 0048678 | 8/2000 |

OTHER PUBLICATIONS

Azmandian et. al., "Towards the Development of an Error Checker for Radiotherapy Treatment Plans: A Preliminary Study", Phys. Med. Biol 52 (2007) 6511-6524.*
Kutcher et. al., "Comprehensive QA for Radiation Oncology: Report of AAPM Radiation Therapy Committee Task Group 40", Med. Phys. Vo 21 No. 4 Apr. 1, 1994 pp. 581-618.*

(Continued)

*Primary Examiner* — David A Vanore
*Assistant Examiner* — David E Smith
(74) *Attorney, Agent, or Firm* — Cozen O'Connor

(57) ABSTRACT

The system for irradiating patients with charged particles includes a raster scanning irradiation unit with a particle accelerator, a beam guide unit, and a 3D scanning system. It also contains a therapy planning system for generating therapy planning data, which include the energy and number of charged particles per raster point in each layer as derived from the derived dose distribution; a therapy control system, which converts the planning data generated by the therapy planning system into irradiation data and irradiation commands for the particle accelerator, the beam guide unit, and the 3D scanning system. The system further has a plurality of safety devices for ensuring that the therapy planning data have been converted correctly and for verifying the functionality of the system. The plurality of safety devices includes an evaluation unit, which checks the irradiation data and irradiation commands supplied by the therapy control system to the 3D scanning system to verify their therapy-specific plausibility.

11 Claims, 10 Drawing Sheets

OTHER PUBLICATIONS

Azmandian et al., "Towards the Development of an Error Checker for Radiotherapy Treatment Plans: a Preliminary Study", Phys. Med. Biol 52 (2007) 6511-6524.*

XP-000953664 Kutcher et al. "Comprehensive QA for Radiation Oncology: Report of AAPM Radiation Therapy Committee Task Group 40" Med. Phys., Vo. 21, No. 4 Apr. 1, 1994 pp. 581-618 ISSN: 0094-2405.

XP-000936499 Jaekel et al. "Quality Assurance for a Treatment Planning System in Scanned Ion Beam Therapy" Med. Phys. 27(7) Jul. 1, 2000 pp. 1588-1600 ISSN: 0094-2405.

XP-020127240 Fatemeh et al. "Towards the Development of an Error Checker for Radiotherapy Treatment Plans: A Preliminary Study", Physics in Medicine and Biology 52 (2007) Nov. 7, 2007 pp. 6511-6524 ISSN: 0031-9155.

* cited by examiner

| Index | Magnet X | Magnet Y | Number of particles (cumulative) | Energy (MeV) | ... |
|---|---|---|---|---|---|
| 1 | -100 | -100 | 50 | 160 | |
| 2 | -50 | -100 | 125 | 160 | |
| 3 | 0 | -100 | 175 | 160 | |
| 4 | 50 | -100 | 225 | 160 | |

IRRADIATION SYSTEM AND IRRADIATION METHOD

BACKGROUND OF THE INVENTION

1. Field of the Invention

The present invention pertains to a system for irradiating patients with charged particles and to a method for monitoring the system.

2. Description of the Related Art

Irradiation systems that irradiate using charged particles offer considerable advantages over conventional irradiation systems which work with x-rays or photon beams. These advantages include the greater accuracy with which the administered dose can be targeted and the decrease in the severity of the side effects on healthy tissue.

Conventional photon beams penetrate the body, but they are also absorbed during their interaction with the molecules of the body and thus undergo a continuous loss of intensity. The maximum dose is present just under the skin, as can be seen from dose-distribution curve A in FIG. 1. This effect is based on the "recruiting" of stray radiation, which occurs after the beam has reached a point just under the skin. As the beam proceeds onward toward the tumor area Z, the radiation dose then decreases in accordance with an exponential curve. A deep tumor thus receives less of the dose than the healthy tissue located in the path of the beam in front of the tumor, and even the organs situated behind the tumor still receive a considerable dose of radiation.

In contrast, charged particles such as protons and heavy ions lose relatively little energy at first, i.e., just after entering the body, but then they are decelerated by repeated interactions with matter (see FIG. 2). The slower the particles become, the more energy they give off and the more they are decelerated. This leads to an "energy explosion" at the end of the particle path, the so-called "Bragg peak" (dose-distribution curve B in FIG. 2). The dose of charged particles in front of the tumor is much smaller than that delivered by irradiation with photons, and the greater part of the dose is thus concentrated in the tumor. In the case of protons, the patient actually remains free of the radiation behind the tumor. Through proper control of the generated particle velocity in coordination with the scanning method, this physical phenomenon makes it possible to deliver the dose into the tumor three-dimensionally. The Bragg peak is so sharp that it must be moved not only laterally over the tumor but also in the depthwise direction through variation of the particle velocity, as can be seen in FIG. 3, which shows a Bragg plateau C.

A preferred scanning method is the so-called "raster scanning method", in which the Bragg peak of the beam of charged particles travels across the tumor under computer control with millimeter accuracy in a three-dimensional grid preestablished by various diagnostic and irradiation planning procedures. According to this method, the beam, which typically has a diameter of 10 mm FWHM (full width at half maximum), is aimed at the individual raster points one after the other, each point thus being exposed typically for 60-90 seconds to the specifically selected dose in each irradiation session. A patient treatment takes place over the course of several of these irradiation sessions on successive days.

Especially in cases of tumors located close to healthy structures vital to life and of very deep tumors, which in many cases cannot be treated with conventional photon beam therapy at all because of the unavoidable, undesirable damage to healthy tissue or which in other cases cannot be treated with conventional photon beam therapy except at very high risk, irradiation with charged particles represents a significant advance in the area of cancer treatment.

When charged particles are used to irradiate patients according to the raster scanning method, the sharp, concentrated dose distribution of the pencil beam explained above and the associated accurately targeted three-dimensional irradiation also impose additional requirements on the accuracy which must be maintained.

For this reason, systems for irradiating patients with charged particles comprise a plurality of safety devices for checking the therapeutic planning data and the functionality of the system, so that incorrectly calculated therapy planning data and data transmission errors between the individual components of the system can be minimized. Thus even isolated data corruption (random errors), which can also have highly disadvantageous effects on the results of the irradiation treatment, can be excluded even more effectively.

SUMMARY OF THE INVENTION

It is an object of the present invention to provide a system for irradiating patients with charged particles which creates an additional and even more efficient redundancy with respect to safety measures, namely, a redundancy which makes it possible for the clinical user to obtain transparent access to the monitored data and by means of which, in addition, the risk of isolated corruption of the data on which the treatment is based can be minimized immediately prior to the irradiation, and to provide a corresponding method for monitoring the system for irradiating patients with charged particles.

According to an aspect of the invention, the system for irradiating patients with charged particles comprises a raster scanning irradiation unit, which comprises a particle accelerator, a beam guide unit, and a 3D scanning system, wherein the 3D scanning system comprises an energy variation unit for setting the energy of the particle beam and thus the penetration depth of the beam into the patient in the beam direction and a deflecting unit with several deflecting magnets for the two-dimensional deflection of the beam between individual raster points in each layer of predefined penetration depth in the patient—layers which are defined by the energy variation unit and which are situated transversely to the beam direction. In addition, the system comprises a therapy planning system for generating therapy planning data, which comprise the energy and number of charged particles for each raster point in each layer as derived from the desired dose distribution, and a therapy control system, which converts the therapy planning data generated by the therapy planning system into irradiation data and irradiation commands for the particle accelerator, the beam guide unit, and the 3D scanning system. Finally, the system comprises a plurality of safety devices for ensuring that the therapy planning data have been converted correctly and for verifying the functionality of the system, these devices comprising an evaluation unit, which checks the irradiation data and the irradiation commands supplied by the therapy control system to the 3D scanning system to verify their therapy-specific plausibility.

As a result, an additional safety component is instrumentalized, which can recognize isolated data corruption in the irradiation data and irradiation commands immediately prior to the irradiation and thus increase the safety of the system even more. In particular, the clinically determined relationships are used to conduct a rapid and efficient plausibility check and thus to increase the safety of the treatment.

The corresponding method for monitoring a system for irradiating patients with charged particles comprises the following steps:

providing a raster-scanning irradiation unit, which comprises a particle accelerator, a beam guide unit, and a 3D scanning system, wherein the 3D scanning system comprises an energy variation unit for setting the energy of the particle beam and thus the penetration depth of the beam into the patient in the beam direction, and a deflecting unit with several deflecting magnets for the two-dimensional deflection of the beam between individual raster points in each of the layers of predetermined penetration depth in the patient, which layers are defined by the energy variation unit and are oriented transversely to the beam direction;

generating therapy planning data in a therapy planning system, wherein the therapy planning data comprise the energy and number of charged particles for each raster point in each layer as derived from the desired dose distribution;

converting the therapy planning data generated by the therapy planning system into irradiation data and irradiation commands for the particle accelerator, the beam guide unit, and the 3D scanning system by means of a therapy control system for irradiating patients; and checking the therapy planning data to ensure that they have been converted correctly and to verify the functionality of the system by means of a plurality of safety devices. Here the checking of the correct conversion of the therapy planning data and the verification of the functionality of the system comprise the checking of the irradiation data and irradiation commands supplied by the therapy control system to the 3D scanning system by means of an evaluation unit to verify their therapy-specific plausibility.

The evaluation unit is preferably located either in a scanning control module, which forms a part of the 3D scanning system and is suitable for receiving the irradiation data and irradiation commands supplied by the therapy control system, or between the therapy control system and the scanning control module. The evaluation unit examines a data file containing the irradiation data and irradiation commands generated by the therapy control system to verify their therapy-specific plausibility and generates a message concerning the result of this examination. Because the evaluation unit is installed immediately upstream of the actual particle application, it is possible to run a direct and reliable final check of the irradiation data and the irradiation commands supplied to the 3D scanning system to verify their therapy-specific plausibility.

In a first examination method, the evaluation unit checks the data file containing the irradiation data and the irradiation commands generated by the therapy control system to verify their therapy-specific plausibility with respect to allowed energy ranges of the charged particles. These energy ranges are either established in advance or determined by the therapy planning data. As a result, unallowed or prohibited energy ranges for the application are excluded.

The raster scanning irradiation unit is preferably equipped with a rotatable gantry, and the evaluation unit checks the data file containing the irradiation data and the irradiation commands generated by the therapy control system to verify their therapy-specific plausibility with respect to allowed gantry angles for the administration of the charged particles. Thus, it is possible in a simple way to prevent the gantry from being set to an incorrect angle. The allowed gantry angles can be defined both by user-specific input values and by a range preestablished by therapy planning.

In another examination stage, the evaluation unit checks the file containing the irradiation data and the irradiation commands generated by the therapy control system to verify their therapy-specific plausibility with respect to the number of charged particles to be administered per raster point.

The number of charged particles per raster point can be compared with a preestablished maximum limit value, which may not be exceeded. The average number of charged particles per raster point can also be compared with conventional values. In this way, it is possible during the final check to exclude an overdose at individual raster points.

The course of the irradiation process always takes place in a predetermined sequence, which is preestablished on the basis of logical ordering principles. The evaluation unit preferably also examines the file containing the irradiation data and the irradiation commands generated by the therapy control system to verify their therapy-specific plausibility with respect to these predetermined logical ordering principles.

These principles include the strictly decreasing monotonicity of the energy values of the charged particles to be administered between the individual irradiation layers, which monotonicity corresponds to the decreasing penetration depth between the individual layers to be traversed during the scanning process. The strictly decreasing monotonicity of the energy values of the charged particles to be administered can be checked by the evaluation unit. By means of an examination of this type, it is possible to exclude errors in the penetration depth of the particle beam for each layer.

Also falling into the category is the checking, by the evaluation unit, of the sequence and arrangement of the raster points for each layer to be scanned during the scanning process. The evaluation unit derives the x values and the y values for all the raster points of a layer of predetermined penetration depth which are to be hit by the treatment beam, determines from them the progression from one raster point to another in the sequence of administration (or, in other words, the course according to which the individual raster points within the two-dimensional arrangement are targeted one after the other) and checks this progression against predetermined criteria. Such criteria are, for example, the presence of raster points which do not lie on the predetermined raster, overly large jumps in the x direction or y direction, etc. By means of this checking process, individual outliers can be easily detected and excluded.

The evaluation unit derives the x values and y values for all of the raster points preferably from the magnet currents supplied to the deflecting magnets of the deflecting unit.

Another form of checking, according to which all of the irradiation data and irradiation commands supplied by the therapy control system to the 3D scanning system for an irradiation session are stored in the evaluation unit and, on the next day, are compared with the entire set of new irradiation data and irradiation commands supplied by the therapy control system to the 3D scanning system for the next irradiation session, is especially preferred. Because therapy plans usually provide completely identical irradiation plans for all the sessions, it is possible in this way to determine very easily the deviations which can occur primarily as a result of changes in external influences such as temperature, air pressure, configuration parameters of the system, etc.

The checking methods described above offer the particular advantage that they do not require large amounts of computing work or time and therefore make it possible to check immediately the irradiation data and the irradiation commands supplied by the therapy control system to the 3D scanning system. In a more highly elaborated application, the evaluation unit can back-calculate a raster-dose distribution from the number and energy of the charged particles to be applied to each raster point and to check this distribution against preestablished criteria to verify their therapy-specific plausibility. The computing effort associated with this is considerable, however, but in this way it is possible to determine very accurately the presence of any holes or islands in the dose distribution over the three-dimensional tumor and then to exclude them.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Additional features and advantages of the present invention can be derived from the following description, which makes reference to the attached drawings.

FIG. 7 shows excerpts of the content of a sample file comprising irradiation data and irradiation commands to be supplied by the therapy control system to the 3D scanning system;

DETAILED DESCRIPTION OF THE PRESENTLY PREFERRED EMBODIMENTS

Figures 1, 2, 3:
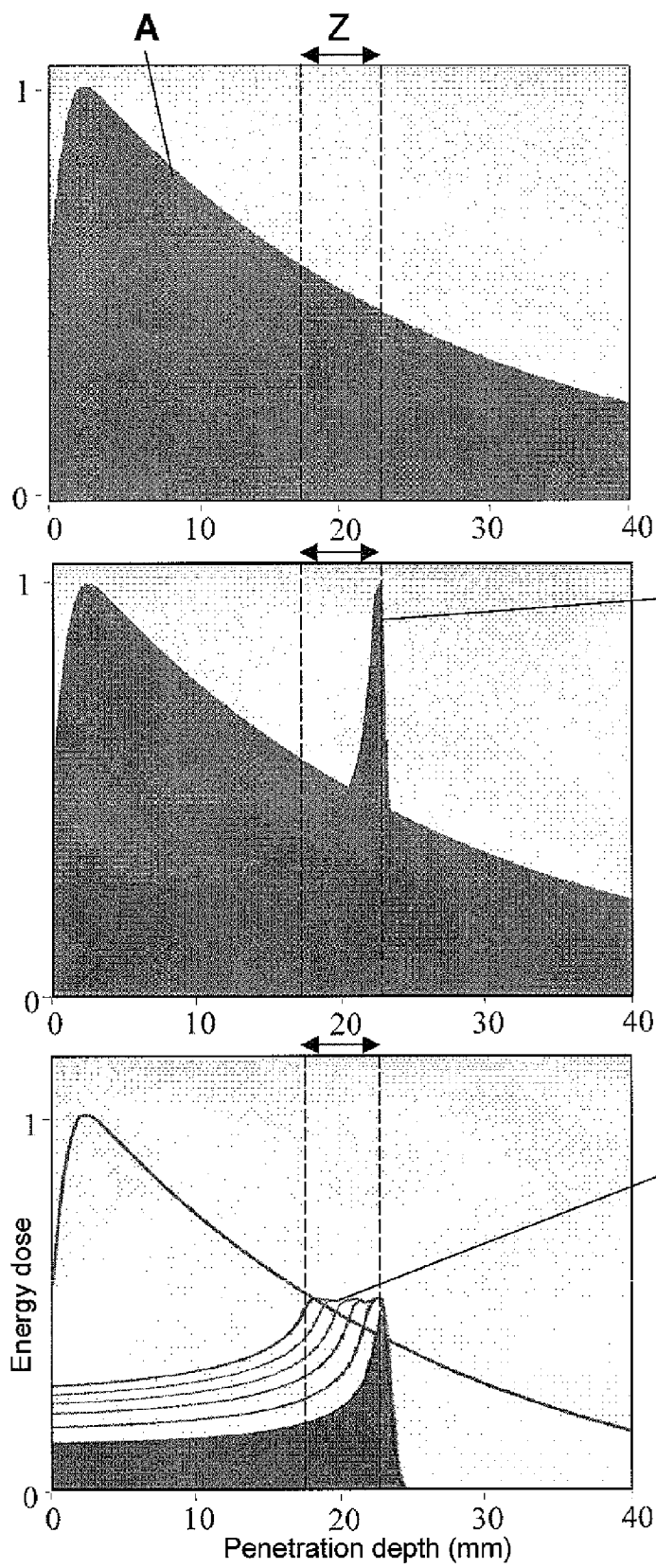
FIG. 1 shows a dose-distribution curve for conventional irradiation with photons.
FIG. 2 shows a dose-distribution curve for irradiation with protons of a certain energy in comparison with the dose-distribution curve for irradiation with photons.
FIG. 3 shows the superimposition of various dose-distribution curves during irradiation with protons for scanning the tumor.
Figure 4:
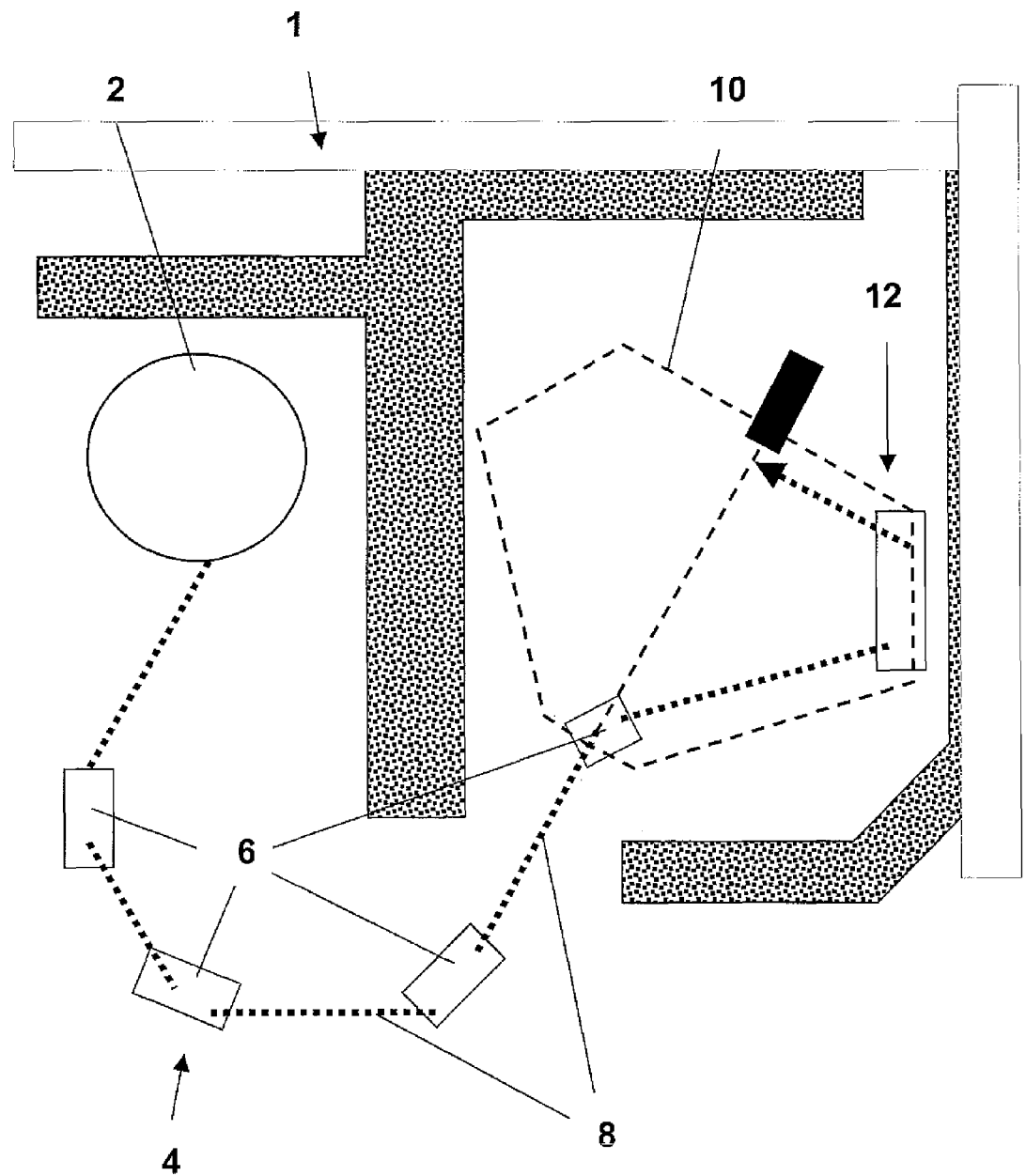
FIG. 4 is a schematic diagram of a system for irradiating patients with charged particles.

To achieve the uniform irradiation profile of tumor tissue in the human body shown in FIG. 3 or a profile which can be adapted as desired, the system for irradiating patients with charged particles according to the invention comprises a raster scanning irradiation unit 1, which is illustrated schematically in FIG. 4. The raster scanning irradiation unit 1 comprises a particle accelerator 2 for charged particles. Protons or heavy ions, for example, can be used as the charged particles for the irradiation of tumors. The raster scanning irradiation unit 1 also comprises a beam guide unit 4, which consists of several beam guide magnets 6 and usually straight beam guide sections 8 arranged between the magnets. One of the most important requirements when irradiating patients with charged particles is that the beam be guided with extreme precision. The particle beam is conducted by the beam guide unit 4 into a treatment room, in which, in the present example, a gantry 10 is arranged, which can be rotated 360°. The 3D scanning system 12 serves to direct the beam accurately onto the tumor tissue and comprises various elements, to be described in greater detail below with reference to FIG. 5, for the precise control of the particle beam.

Figure 5:
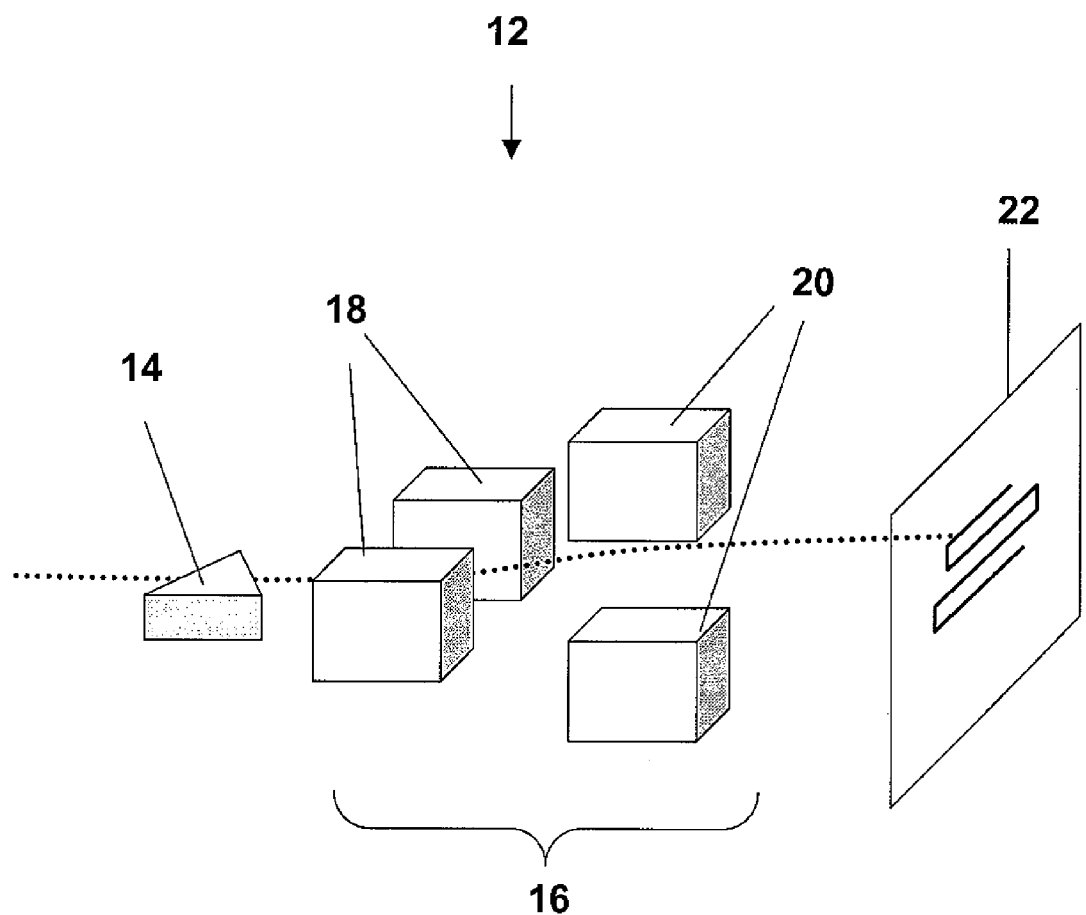
FIG. 5 is a diagram of an exemplary embodiment of the 3D scanning system in isolation.

In the example illustrated in FIG. 5, the deflecting unit 16 of the 3D scanning system 12 is connected to the ring of the gantry 10 and can be rotated together with it into any desired position, from which the patient is then irradiated. As a result, it is possible to irradiate from various directions for various applications. The invention is also applicable to stationary irradiation machines not designed as a gantry 10.

With the inventive system, the patients are preferably irradiated in a raster scanning process, for which purpose the tumor tissue is divided into uniformly spaced raster points 62 (see FIG. 11b), to which the dose is administered, the points being arranged in a three-dimensional raster.

So that the tumor can be scanned accurately with the treatment beam, i.e., so that the particle beam can be directed accurately onto each of the individual 3D raster points 62 in the target volume, the 3D scanning system 12 (see FIG. 5) has, first, an energy variation unit 14 for setting the energy of the particle beam and thus the penetration depth of the beam into the patient in the beam direction. In the present example, the energy variation unit is designed as a degrader wedge, which in a specific case can be pushed a certain distance into the path of the beam, where it will thus absorb a certain amount of the energy of the particle beam. In this way, the energy of the particle beam and thus the penetration depth of the particle beam in the beam direction into the body can be determined with an accuracy on the sub-millimeter scale. In addition to the degrader wedge, it is also possible to use other types of energy variation units 14 such as range shifter plates.

The deflecting unit 16 aims the particle beam at various selected raster points within each layer 22 of predetermined penetration depth in the patient; the layer in question is defined by the energy variation unit 14 and is oriented transversely to the beam direction. The deflecting unit 16 comprises, for example, a double-pole deflecting magnet 18 for deflecting the particle beam in the x direction and a double-pole deflecting magnet 20 for deflecting the particle beam in the y direction. Other arrangements are also conceivable. The deflecting unit 16 thus causes the particle beam to travel along a meandering path in each layer 22 of predetermined penetration depth, wherein the particle beam is always turned off in the sections of the path located between two adjacent raster points 62. To ensure the administration of a precise dose, furthermore, the beam is directed onto the tumor only after the process of adjusting the settings of the deflecting magnets 18, 20 has been completed. The dose or the number of charged particles to be administered to one raster point 62 can differ considerably from that administered to the adjacent point, depending on the shape of the tumor.

Figure 6:
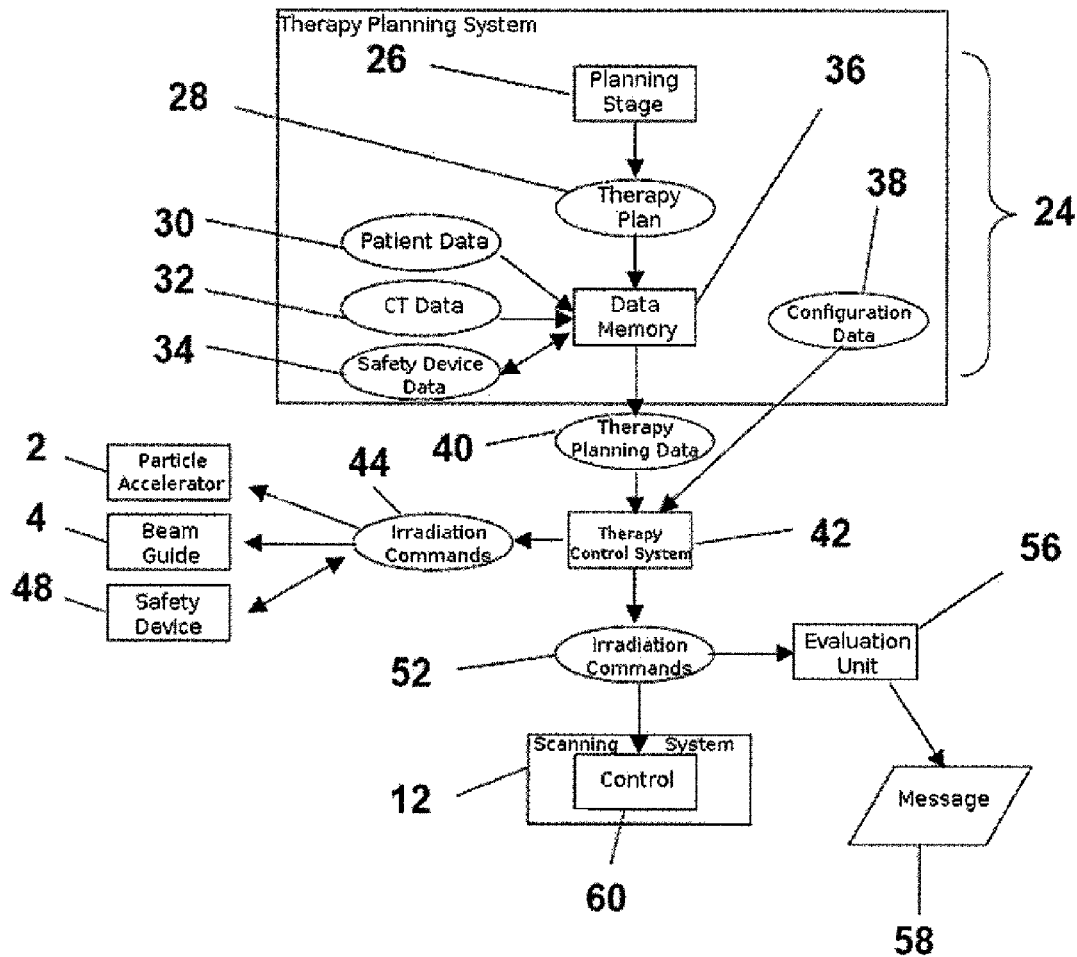
FIG. 6 is a general schematic diagram of the electronic components of a system according to the invention, which components participate in the calculation and transmission of irradiation data and irradiation commands.

A highly complex system which establishes the individual irradiation parameters down to the smallest detail and monitors the functionality of the system is provided for therapy planning and for ensuring precise irradiation. The electronic components of a system according to the invention which participate in the calculation and transmission of the irradiation data and the irradiation commands are illustrated in FIG. 6. The therapy planning system 24 comprises a therapy planning stage 26 for dose calculation and optimization. To this stage flow all the results of the previously completed medical evaluation, the indication, the contouring of the target volume, and the therapy concept as well as the associated CT data. On that basis, the therapy planning stage 26 calculates first the desired dose distribution {x, y, z dose} under consideration of the parameters established by the physician in charge. Then, under consideration of the functional data of the overall system, a therapy plan 28 is generated, which establishes the energy and number of charged particles for each raster point 62 in each layer 22 by calculations based on the desired dose distribution. Thus, a data set of the type {x, y, particle energy, number of particles} is assigned to each raster point 62 in the so-called "spot space". These data of the therapy plan 28 are transmitted to a therapy data memory 36, which also contains all the patient data 30 and the CT data 32 for the purpose of, for example, patient position verification. In addition, safety devices 34, which check the therapy plan in detail, are provided even at this early point.

The therapy planning system 24 then supplies the therapy control system 42 with all of the therapy planning data 40 from, for example, the therapy data memory 36. Configuration data 38 of the system are also taken into account, including specific machine settings and configurations.

The therapy control system 42 converts the therapy planning data 40 generated by the therapy planning system 24 into irradiation commands 44 for the particle accelerator 2 and the beam guide unit 4. All of the machine-relevant data are also checked and monitored continuously in highly engineered safety devices 48. This extends from the monitoring of the doors and the monitoring of the beam to the checking of the sensors (not shown) which check the treatment beam during the irradiation process and which thus represent in themselves yet another safety device.

The therapy control system 42, furthermore, converts the therapy planning data 40 generated by the therapy planning system 24 into irradiation data and irradiation commands 52 for the 3D scanning system 12. A scanning control module 60 suitable for receiving the irradiation data and irradiation commands 52 transmitted by the therapy control system and for taking over the job of aiming the components of the 3D scanning system 12 on the basis of those data and commands is preferably incorporated into the 3D scanning system. According to the invention, an evaluation unit 56, which checks the irradiation data and irradiation commands 52 supplied by the therapy control system 42 to the 3D scanning system 12 before they are actually processed or implemented to verify their therapy-specific plausibility, is installed between the therapy control system 42 and the scanning control module 60 or in the scanning control module 60 itself. This means that the transmitted irradiation data and irradiation commands 52 are examined in an least one respect but preferably with respect to several therapy-specific parameters which ensure a simple but comprehensive plausibility check of the irradiation data and irradiation commands 52 from a clinical standpoint for the specific case in question. This point will be discussed again in greater detail below with reference to FIGS. 7-11.

The evaluation unit 56 is preferably suitable for generating a message 58 concerning the result of the examination, i.e., a message which can serve as the basis for interrupting the treatment or for implementing other adaptive measures.

The irradiation data and irradiation commands 52 transmitted by the therapy control system 42 to the scanning control module 60 are usually contained in a single data file, the content of which is reproduced by way of example in FIG. 7. For example, the irradiation data and irradiation commands 52 can contain the magnet current in the x direction, the magnet current in the y direction, the number of charged particles per raster point 62, and the energy of the particle beam. They can also contain, for example, monitoring limits for the detectors of the 3D scanning system 12 and many other irradiation-specific and irradiation-relevant parameters.

Figure 8:
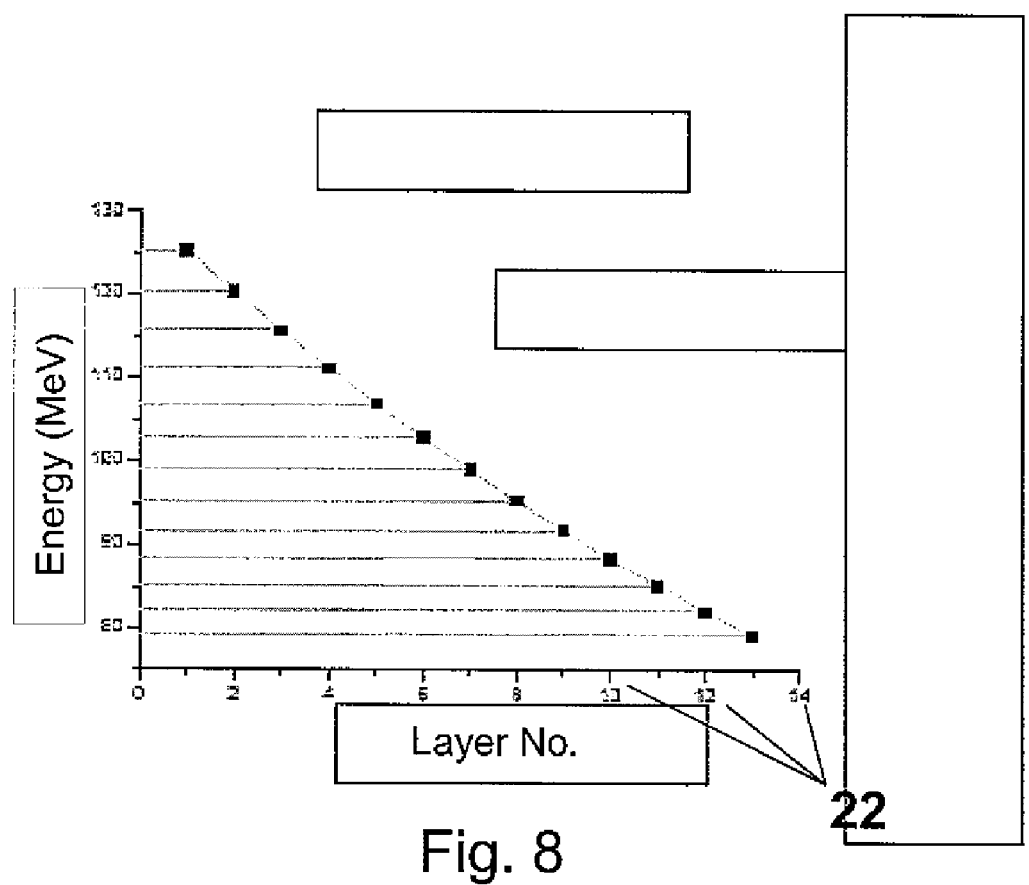
FIG. 8 is a graph illustrating the checking of the irradiation data with respect to the allowed energy ranges of the charged particles in various layers of irradiation depth.
Figure 9:
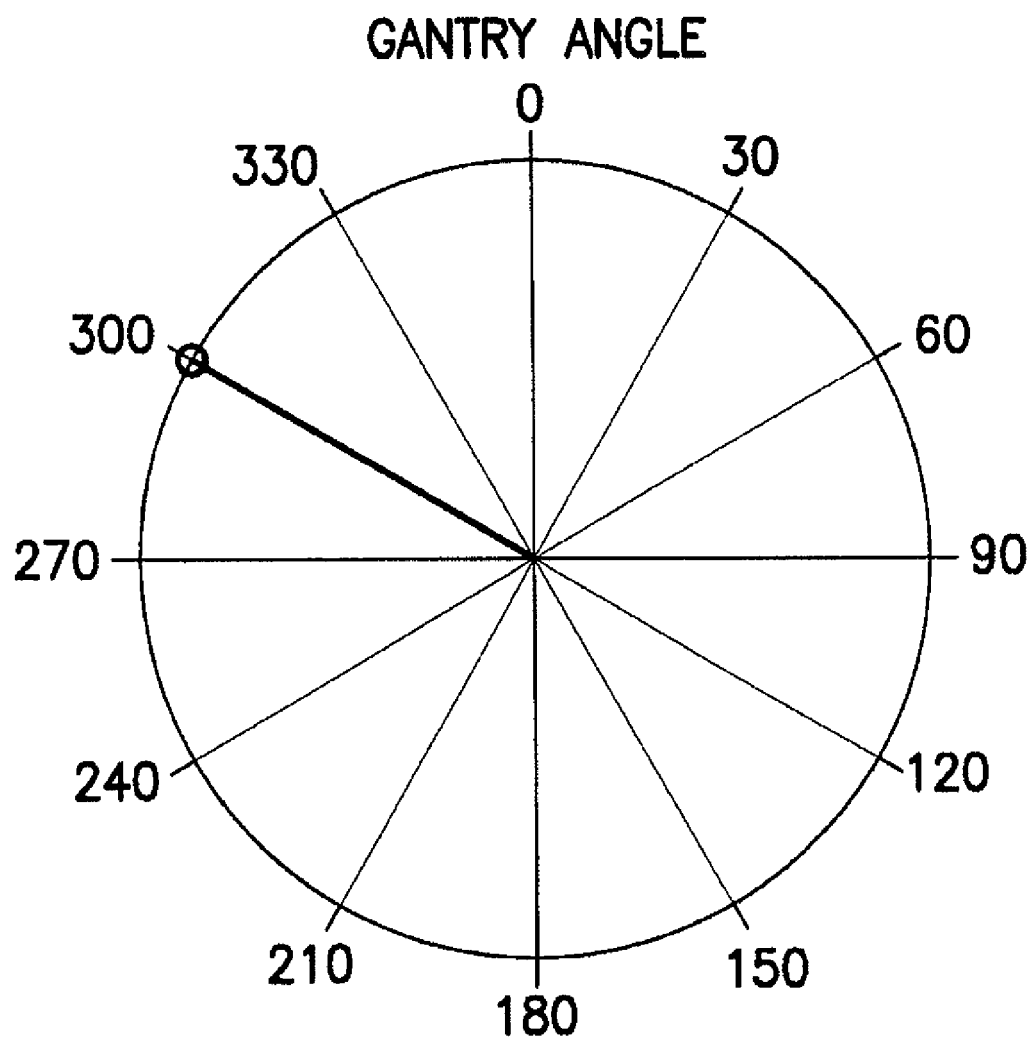
FIG. 9 is a graph illustrating the checking of the irradiation data with respect to allowed gantry angles.

As illustrated in FIG. 8, the evaluation unit 56 now checks, for example, the required energy of the particle beam to make sure that its values are within the range permitted for the specific treatment. Particle energies which are too high or too low can therefore be detected at all times. In a similar manner, the gantry angle (see FIG. 9) can be examined to determine its therapy-specific plausibility for the administration of the charged particles in the specific application.

Figure 10:
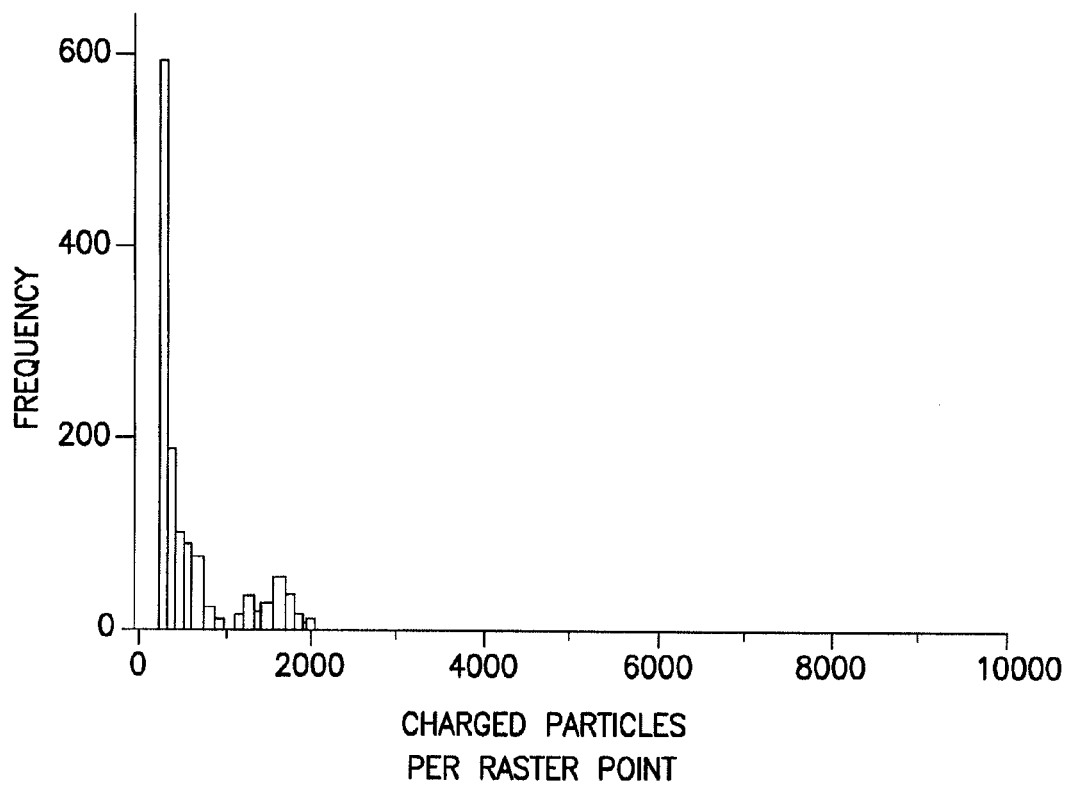
FIG. 10 is a graph illustrating the checking of the irradiation data with respect to the number of particles per raster point to be administered.

It is also helpful to evaluate the therapy-specific plausibility of the irradiation data and the irradiation commands 52 with respect to the number of charged particles to be administered per raster point 62, as shown in FIG. 10. Here, too, certain upper and lower limits can be set, which the clinical user can easily use to verify that the values in question do not exceed or fall below them.

Figure 11A:
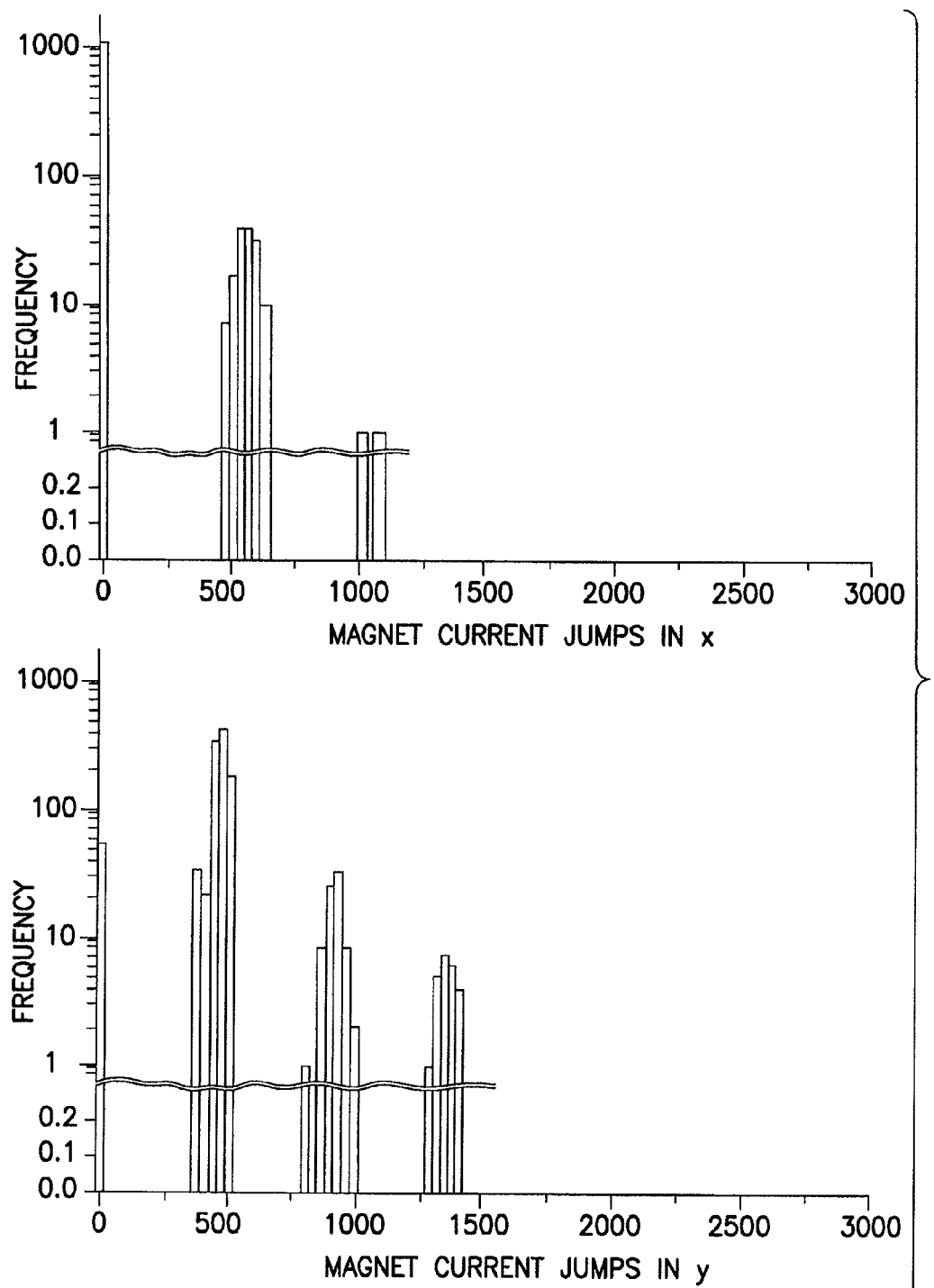
FIG. 11 shows various types of graphs which illustrate the checking of the irradiation data with respect to the sequence and arrangement of the raster points for each layer to be scanned during the scanning process.

FIG. 11*a* shows the jumps in the magnet currents in the x and y directions versus their frequency of occurrence. This type of graph clearly shows the raster settings of the desired irradiation and makes it especially easy to detect deviations, e.g., magnet current jumps located between the desired raster settings of the magnet current or wide outliers.

Another way in which the irradiation data and irradiation commands 52 can be checked is to verify their therapy-specific plausibility with respect to predetermined logical ordering principles. An example of this is to check the energy values of the charged particles to be administered to verify their strictly decreasing monotonicity and thus to verify the continuously decreasing penetration depth between the individual layers 22 to be traversed during the scanning process.

Figure 11B:
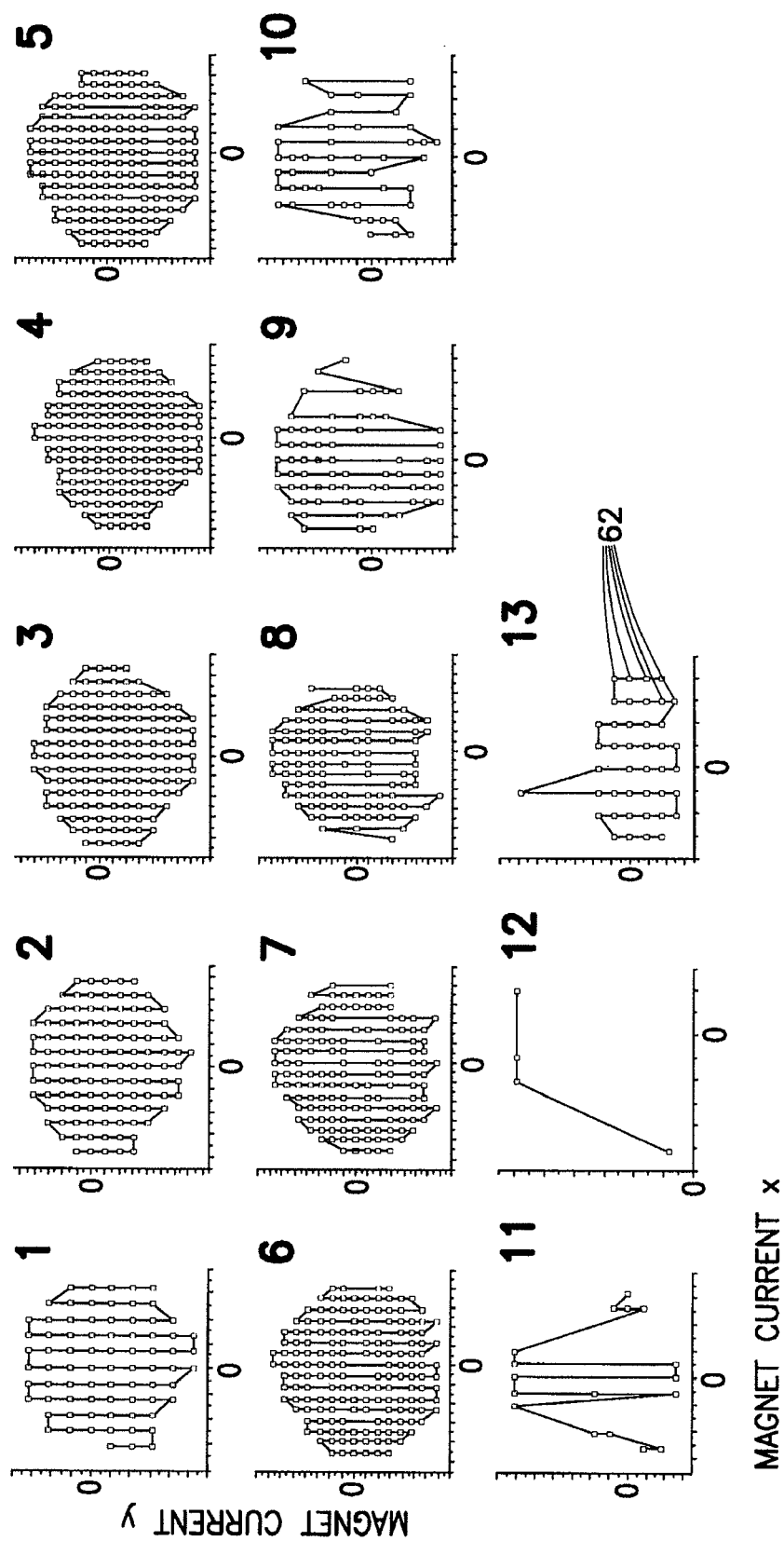

In an especially preferred embodiment, the evaluation unit 56 can also check the sequence and arrangement of the raster points 62 in each layer 22 to be scanned during the scanning process (see FIG. 11*b*). The evaluation unit 56 preferably derives the x values and y values for all raster points 62 of one layer 22 of a predetermined penetration depth which are to be hit by the treatment beam. On this basis, the progression from one raster point 62 to another in the sequence of administration within the two-dimensional arrangement of each layer 22 is determined and this progression is checked against predetermined criteria such as the presence of "island points" or deviations in the systematic irradiation pattern. The evaluation unit 56 derives the x values and the y values for all raster points 62 preferably from the magnet currents of the deflecting magnets 18, 20 of the deflecting unit 16.

In a more highly elaborated embodiment, the evaluation unit 56 calculates a raster-dose distribution from the number and energy of the charged particles to be administered to each raster point 62 and checks this against predetermined criteria to verify its therapy-specific plausibility. This approach requires a very great deal of computing power.

Another form of checking, according to which all of the irradiation data and irradiation commands 52 supplied by the therapy control system 42 to the 3D scanning system 12 for an irradiation session are stored in the evaluation unit 56 and compared on the next day with the entire set of new irradiation data and irradiation commands 52 supplied by the therapy control system 42 to the 3D scanning system 12 for the next irradiation session, is especially preferred. Because therapy plans usually provide completely identical irradiation plans for all sessions, it is especially easy in this way to determine the deviations which can occur primarily as a result of changes in external influences such as temperature, air pressure, configuration parameters of the system, etc.

In all of these variants, the final evaluation of the data automatically acquired by the evaluation unit 56 can be carried out manually by the clinical user or automatically by a computer.

When at least one, preferably, however, several of the above-mentioned checking methods are used, it is possible to instrumentalize not only the already existing efficient safety devices 34, 48 (including the sensors for the treatment beam), but also another function, which checks the irradiation data and irradiation commands 52 supplied by the therapy control system 42 to the 3D scanning system 12 to verify their therapy-specific plausibility for each specific application and thus almost completely excludes even any randomly occurring errors in the irradiation data and irradiation commands 52 under consideration of their clinical relevance.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A system for irradiating a patient with a particle beam of charged particles, comprising:
    a raster scanning irradiation unit, which comprises a particle accelerator, a beam guide unit, and a 3D scanning system, wherein the 3D scanning system comprises an energy variation unit for setting an energy of the particle beam and thus a penetration depth of the particle beam into the patient in a beam direction and a deflecting unit with several deflecting magnets for a two-dimensional deflection of the particle beam between individual raster points in each of several layers of predefined penetration depth in the patient, the layers being defined by the energy variation unit and being situated transversely to the beam direction;
    a therapy planning system for generating therapy planning data, which comprise an energy and number of charged particles for each raster point in each layer as derived from a desired dose distribution;
    a therapy control system, which converts the therapy planning data generated by the therapy planning system into irradiation data and irradiation commands for the particle accelerator, the beam guide unit, and the 3D scanning system; and
    a plurality of safety devices for ensuring that the therapy planning data have been converted correctly and for verifying the functionality of the system;
    wherein the plurality of safety devices comprises an evaluation unit, which checks the irradiation data and irradiation commands supplied by the therapy control system to the 3D scanning system to verify a therapy-specific plausibility of the irradiation data and irradiation commands;
    wherein the evaluation unit checks a sequence and arrangement of the raster points to be hit during a scanning process for each layer by deriving x values and y values for all raster points of one layer of predetermined penetration depth to be hit during a scanning process, determining from them a progression from one raster point to another in a sequence of administration within the two-dimensional arrangement of the raster points, and then checking the progression against predetermined criteria, wherein the evaluation unit derives the x values and the y values for all raster points from values of magnet currents of the deflecting magnets of the deflecting unit, said values of magnet currents being included in the irradiation data and irradiation commands supplied by the therapy control system to the 3D scanning system.

2. The system according to claim 1, wherein the 3D scanning system comprises a scanning control module, which is adapted to receive irradiation data and irradiation commands from the therapy control system.

3. The system according to claim 2, wherein the evaluation unit is arranged between the therapy control system and the scanning control module or in the scanning control module.

4. The system according to claim 1, wherein the evaluation unit is adapted to examine a data file containing the irradiation data and irradiation commands generated by the therapy control system and to generate a message concerning results of the examination.

5. A method for monitoring a system for irradiating a patient with a particle beam of charged particles, comprising:
    providing a raster scanning irradiation unit, which comprises a particle accelerator, a beam guide unit, and a 3D scanning system, wherein the 3D scanning system comprises an energy variation unit for setting an energy of the particle beam and thus a penetration depth of the particle beam into the patient in a beam direction and a deflecting unit with several deflecting magnets for a two-dimensional deflection of the particle beam between individual raster points in several layers of predefined penetration depth in the patient, the layers being defined by the energy variation unit and being situated transversely to the beam direction;
    generating therapy planning data in a therapy planning system, wherein the therapy planning data comprise an energy and number of charged particles for each raster point in each layer as derived from a desired dose distribution;
    converting the therapy planning data generated by the therapy planning system into irradiation data and irradiation commands for the particle accelerator, the beam guide unit, and the 3D scanning system by means of a therapy control system; and
    checking the therapy planning data to ensure that they have been converted correctly and to verify the functionality of the system by means of a plurality of safety devices;
    wherein the checking of the correct conversion of the therapy planning data and the verification of the functionality of the system comprise the checking of the irradiation data and irradiation commands supplied by the therapy control system to the 3D scanning system by means of an evaluation unit to verify a therapy-specific plausibility of the irradiation data and irradiation commands;
    wherein the evaluation unit checks a sequence and arrangement of the raster points to be hit during a scanning process for each layer by deriving x values and y values for all raster points of one layer of predetermined penetration depth to be hit during a scanning process, determining from them a progression from one raster point to another in a sequence of administration within the two-dimensional arrangement of the raster points, and then checking the progression against predetermined criteria, wherein the evaluation unit derives the x values and the y values for all raster points from values of magnet currents of the deflecting magnets of the deflecting unit, said values of magnet currents being included in the irradiation data and irradiation commands supplied by the therapy control system to the 3D scanning system.

6. The method according to claim 5, wherein the evaluation unit, which is installed either in a scanning control module or between the therapy control system and the scanning control module, examines a data file containing the irradiation data and irradiation commands generated by the therapy control system to verify their therapy-specific plausibility and generates a message concerning results of the examination.

7. The method according to claim 6, wherein the evaluation unit checks the data file containing the irradiation data and irradiation commands generated by the therapy control system to verify their therapy-specific plausibility with respect to permitted energy ranges of the charged particles.

8. The method according to claim 6, wherein the raster scanning irradiation unit comprises a rotatable gantry, and the evaluation unit checks the data file containing the irradiation data and irradiation commands generated by the therapy control system to verify their therapy-specific plausibility with respect to permitted gantry angles for administering the charged particles.

9. The method according to claim 6, wherein the evaluation unit checks the data file containing the irradiation data and irradiation commands generated by the therapy control system to verify their therapy-specific plausibility with respect to a number of the charged particles to be administered per raster point.

10. The method according to claim 5, wherein the evaluation unit checks a strictly decreasing monotonicity of energy values of the charged particles to be administered to verify a decreasing penetration depth between the individual layers to be traversed during a scanning process.

11. The method according to claim 5, wherein all of the irradiation data and irradiation commands supplied by the therapy control system to the 3D scanning system for an irradiation session are stored in the evaluation unit and are compared with an entire set of new irradiation data and irradiation commands supplied by the therapy control system to the 3D scanning system for a following irradiation session.

* * * * *